United States Patent [19]
Salas et al.

[11] Patent Number: 5,945,085
[45] Date of Patent: Aug. 31, 1999

[54] AEROSOL DEODORANT-ANTIPERSPIRANT PRODUCT

[75] Inventors: Lucia Salas, North Bergen, N.J.; Wolfgang R. Bergmann, Long Grove, Ill.

[73] Assignee: Church & Dwight Co., Inc., Princeton, N.J.

[21] Appl. No.: 08/878,764

[22] Filed: Jun. 19, 1997

[51] Int. Cl.$^6$ .............................. A61K 7/32; A61K 9/12
[52] U.S. Cl. .............................. 424/45; 424/65; 424/47; 424/66; 424/67; 424/68; 424/69
[58] Field of Search .................... 424/65, 45, 47, 424/66, 67, 68

[56] References Cited

U.S. PATENT DOCUMENTS

| | | | |
|---|---|---|---|
| 3,088,874 | 5/1963 | Geary et al. | 167/32 |
| 3,317,372 | 5/1967 | Hart | 167/14 |
| 3,920,807 | 11/1975 | Curry et al. | 424/46 |
| 3,968,203 | 7/1976 | Spitzer et al. | 424/47 |
| 4,045,548 | 8/1977 | Luedders et al. | 424/47 |
| 4,183,911 | 1/1980 | Smithies et al. | 424/36 |
| 4,278,658 | 7/1981 | Hooper et al. | 424/65 |
| 4,352,789 | 10/1982 | Thiel | 424/46 |
| 4,382,079 | 5/1983 | Marschner | 424/65 |
| 4,450,151 | 5/1984 | Shinozawa | 424/46 |
| 4,534,962 | 8/1985 | Marschner | 424/65 |
| 4,548,808 | 10/1985 | Chavkin | 424/47 |
| 4,659,560 | 4/1987 | Bews et al. | 424/47 |
| 4,675,177 | 6/1987 | Geary | 424/47 |
| 4,695,451 | 9/1987 | Straw et al. | 424/47 |
| 4,740,366 | 4/1988 | Winston et al. | 424/45 |
| 4,743,440 | 5/1988 | Callingham et al. | 424/46 |
| 4,822,602 | 4/1989 | Sabatelli | 424/65 |
| 4,832,945 | 5/1989 | Osipow et al. | 424/65 |
| 4,840,786 | 6/1989 | Johnson et al. | 424/43 |
| 4,851,212 | 7/1989 | Winston et al. | 424/45 |
| 4,863,721 | 9/1989 | Beck et al. | 424/47 |
| 4,889,711 | 12/1989 | Kai et al. | 424/47 |
| 4,904,463 | 2/1990 | Johnson et al. | 424/44 |
| 4,935,224 | 6/1990 | Russo et al. | 424/47 |
| 5,114,717 | 5/1992 | Kuznitz et al. | 424/401 |
| 5,156,833 | 10/1992 | Osugi et al. | 424/46 |
| 5,156,834 | 10/1992 | Beckmeyer et al. | 424/47 |
| 5,178,871 | 1/1993 | Thill | 424/405 |
| 5,194,262 | 3/1993 | Goldberg et al. | 424/401 |
| 5,281,409 | 1/1994 | Thayer et al. | 424/47 |
| 5,368,842 | 11/1994 | Lederman et al. | 424/47 |

FOREIGN PATENT DOCUMENTS

| | | |
|---|---|---|
| 0 485 012 | 10/1991 | European Pat. Off. . |
| 1476117 | 6/1975 | United Kingdom . |

*Primary Examiner*—Raj Bawa
*Attorney, Agent, or Firm*—Irving Fishman

[57] ABSTRACT

This invention provides a deodorant-antiperspirant composition in a dispensing container pressurized with an aerosol propellant. The primary ingredients of a typical product are particulate sodium bicarbonate, particulate antiperspirant astringent salt, volatile silicone oil, carboxylate ester emollient, and a suspending agent such as hydrophobic hectorite clay. An invention aerosol deodorant-antiperspirant product has a stable particulate sodium bicarbonate and astringent salt suspension phase. The odor and wetness reduction properties of the product during underarm application are enhanced by the micronized form of the astringent salt ingredient, and by the controlled ratio of volatile oil to emollient in the product.

26 Claims, No Drawings

1

AEROSOL DEODORANT-ANTIPERSPIRANT PRODUCT

BACKGROUND OF THE INVENTION

This invention generally relates to cosmetic products having deodorant and antiperspirant activities. More specifically this invention relates to nonaqueous aerosol deodorant-antiperspirant compositions having a bicarbonate salt content.

Sodium bicarbonate long has been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective composition in cosmetic product form which has a deodorization capacity, and which is capable of consumer acceptability, presents many factors which are unique. Because sodium and potassium bicarbonate have only limited solubility in water, alcohol and other solvents, the preparation of a composition suitable for dispensing in cosmetic product form has involved many processing obstacles. In addition to the problem of limited solubility, sodium bicarbonate often is incompatible with other ingredients of conventional cosmetic formulations.

Other limiting factors are described in references such as U.S. Pat. No. 4,534,962. Sodium bicarbonate in solution undergoes persistent degradation into carbon dioxide and sodium carbonate (a known skin irritant). Because alkali metal bicarbonate has solubility limitations, a proportionally larger amount of water is required for higher bicarbonate salt levels in cosmetic products. Consequently less alcohol is permitted, which results in a cool wet feel on skin, and slow drying of an applied cosmetic product.

Other product developments include aerosol suspensions which are sprayed from a pressurized container having a content of particulate sodium bicarbonate slurried with a liquid propellant medium. Alkali metal bicarbonate in a propellant-soluble vehicle such as ethanol (0.3–15 weight percent) with about 90% propellant is described in British Patent 1,476,117.

The difficulties encountered with aerosol suspensions of sodium or potassium bicarbonate include the settling and/or agglomeration of the particulate suspension phase, clogging of the dispensing nozzle, a non-uniform spray pattern, nonadherence of the particulate bicarbonate deodorant to the sprayed skin area, and an overly wet spray which requires an extended drying time.

Other cosmetic products have been developed which exhibit antiperspirant activity against underarm wetness in human subjects. An antiperspirant is applied to suppress perspiration and prevent offensive odors such as an axillary odor caused by decomposition of sweat. A popular type of antiperspirant cosmetic product is a nonaqueous aerosol formulation which contains an antiperspirant-active ingredient such as aluminum chlorohydrate, a carrier such as talc, an oil component to deposit and retain the antiperspirant-active ingredient on a skin surface, and a liquid propellant medium. One disadvantage of nonaqueous aerosol antiperspirant products is the tendency for dust cloud formation which the aerosol medium is dispensed from a pressurized container.

There is continuing interest in the development of cosmetic products which have a high level of consumer acceptance.

Accordingly, it is an object of this invention to provide an improved cosmetic product which is composed of a non-aqueous liquid medium having effective quantities of deodorant-active and antiperspirant-active ingredients.

It is another object of this invention to provide an aerosol deodorant-antiperspirant composition which is a liquid solution of organic ingredients and propellant medium, and which has a dimensionally stable suspension phase of particulate alkali metal bicarbonate ingredient and particulate antiperspirant salt ingredient.

Other objects and advantages of the present invention shall become apparent from the accompanying description and examples.

DESCRIPTION OF THE INVENTION

One or more objects of the present invention are accomplished by the provision of a deodorant-antiperspirant composition in an aerosol dispensing container which comprises (1) between about 1–15 weight percent of particulate alkali metal bicarbonate having an average particle size between about 5–100 microns; (2) between about 5–25 weight percent of particulate antiperspirant ingredient having an average particle size between about 1–40 microns; (3) between about 10–25 weight percent of volatile oil; (4) between about 5–20 weight percent of emollient, and the ratio of volatile oil to emollient is between about 1–2.5:1; (5) between about 0.5–3 weight percent of particulate suspending agent; and (6) between about 10–60 weight percent of aerosol propellant.

An invention aerosol deodorant-antiperspirant product normally is in a substantially anhydrous state, since the presence of water tends to destabilize the particulate suspension phase, in addition to other disadvantages such as an undesirable wet feel when the aerosol product is applied to the underarm of a human subject.

A deodorizing effective quantity of particulate alkali metal bicarbonate is suspended in the aerosol liquid medium of an invention aerosol product. The alkali metal bicarbonate preferably is sodium or potassium bicarbonate or a mixture thereof.

The bicarbonate salt ingredient typically can have an average particle size between about 10–250 microns. In a preferred embodiment the bicarbonate ingredient is in micronized form, and has an average particle size between about 0.5–20 microns.

The present invention also contemplates the use of alkali metal bicarbonate in the form of particles which are encapsulated with an organic surface coating. An invention aerosol deodorant-antiperspirant product can have a suspension phase which contains both encapsulated and unencapsulated particles of alkali metal bicarbonate. The said bicarbonate mixture provides both immediate and long term deodorizing activities when sprayed on the underarm surface of a human subject.

The alkali metal bicarbonate core matrix of organic-encapsulated particles is sodium bicarbonate or potassium bicarbonate or a mixture thereof. The average particle size of the encapsulated alkali metal bicarbonate ingredient can range between about 20–200 microns. The organic encapsulant of the coated particles typically comprises between about 5–60 weight percent of the encapsulated alkali metal bicarbonate particles.

The organic encapsulant of the coated particles is selected from hydrophilic and hydrophobic (water-insoluble) film-forming agents, and mixtures thereof, such as hydrocolloids and polysaccharides.

The term "hydrophilic" as employed herein refers to an encapsulant film-forming agent which has a water-solubility of at least about two grams per one hundred grams of water at 25° C.

The organic encapsulant can consist of 100% hydrophilic encapsulant, or 100% water-insoluble encapsulant, or any mixture thereof. The rate of alkali metal bicarbonate release after aerosol spraying on a skin surface is directly related to the hydrophilicity of the encapsulant coating on the alkali metal bicarbonate particles. A hydrophilic encapsulant coating will sustain-release the core alkali metal bicarbonate content at a faster rate than a water-insoluble encapsulant coating. An organic encapsulant can comprise a hydrophilic polymer having a content between about 5–80 weight percent of a water-insoluble polymer.

Suitable hydrophilic encapsulants for coating the alkali metal bicarbonate particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene oxide, polyvinyl alcohol/acetate, and the like. Polyvinyl acetate is illustrative of a water-insoluble polymer which can be included as an additional coating component to moderate the hydrophilicity of a hydrophilic polymer coating.

Suitable water-insoluble encapsulants include polyvinyl acetate, polyacrylamide, polyvinyl chloride, polystyrene, polyethylene, polyurethane, polymethacrylate, paraffin wax, carnauba wax, beeswax, stearyl alcohol, zein, shellac, edible fat, and the like.

The encapsulant can be applied to the alkali metal bicarbonate particles by conventional coating means, such as rotating disk, fluidized bed, spray drying, freeze drying, tumbling, coacervation, and the like.

The antiperspirant ingredient of a present invention aerosol deodorant-antiperspirant composition typically is a particulate astringent compound which has an average particle size between about 10–35 microns. Superior wetness reduction properties are obtained if part or all of the antiperspirant ingredient is in the form of particles which have a diameter less than about 15 microns. The Examples demonstrate the beneficial effect of ultrafine antiperspirant particles on underarm wetness reduction. Optionally, the antiperspirant ingredient can be pre-coated with a polymer to prevent interaction with the other ingredients, and to provide a sustained-release antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium tetrachlorohydrex glycine. Aluminum-zirconium tetrachlorohydrex glycine is commercially available as Rezal 36 GP Superultrafine (Reheis), and Reach AZP 908 (Reheis).

The volatile oil ingredient of an invention aerosol deodorant-antiperspirant composition preferably is selected from silicone and branched-chain hydrocarbon compounds.

A volatile silicone oil ingredient can be a cyclic or linear polydimethylsiloxane containing between about 3–9 silicon atoms. A suitable cyclic volatile polydimethylsiloxane compound is illustrated by the formula:

$$\left[ \begin{array}{c} CH_3 \\ | \\ [Si-O]_n \\ | \\ CH_3 \end{array} \right]$$

where n is an integer with a value of about 3–7.

A suitable linear polydimethylsiloxane is illustrated by the formula:

$$(CH_3)_3Si-O[Si(CH_3)_2-O]_n-Si(CH_3)_3$$

where n is an integer with a value of about 1–7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 245 Fluid (Dow Corning) is a cyclic volatile silicone which is commercially available. *CTFA Cosmetic Ingredient Dictionary,* Third Edition, (Estrin et al., Editors; The Cosmetic, Toiletry and Fragrance Association, Inc.; 1982) lists cyclic silicones on page 60, under the entry "cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Parmethyl 101A and Permethyl 102A.

An emollient is included as an essential ingredient in a present invention aerosol deodorant-antiperspirant composition, and it is employed in a balanced ratio relative to the volatile oil ingredient. An optimal underarm wetness reduction effect is obtained when the ratio of volatile oil to emollient is between about 1–2.5:1, as demonstrated by the comparative data in the Examples.

Suitable organic compounds having utility as an emollient ingredient include carboxylate esters such as lactates, citrates, tartrates and adipates; fatty alcohols, fatty acids and fatty esters; mineral oils; nonvolatile silicones; alkylene glycols and polyalkylene glycols; lanolin and lanolin esters; and the like. A carboxylate ester such as diisopropyl adipate is a preferred type of emollient in an invention aerosol deodorant-antiperspirant composition.

Another essential ingredient of an invention aerosol deodorant composition is between about 0.5–3 weight percent of a suspending agent in particle form.

Suitable suspending agents include colloidal silica such as pyrogenic silica having a particle size range between about 0.001–0.03 micron; colloidal alumina; hydrophobic powders such as montmorillonite clays (e.g., bentonites and hectorites) which are surface-treated with a cation surfactant such as ditallow dimethyl ammonium chloride (e.g., quaternium 18 hectorite; Bentone 38 by Rheox, Inc.).

Other suitable suspending agents are described in publications such as British 1,476,117; U.S. Pat. No. 4,045,548; and U.S. Pat. NO. 4,904,463; incorporated by reference.

The propellant ingredient of an invention aerosol deodorant-antiperspirant composition is a liquified normally-gaseous medium preferably selected from the group consisting of hydrocarbons and halogenated hydrocarbons and mixtures thereof. A typical aerosol propellant is one selected from the group consisting of $C_3$–$C_5$ aliphatic hydrocarbons and mixtures thereof.

Suitable aerosol propellants are described in publications such as U.S. Pat. Nos. 3,968,203; 4,889,711; 4,935,224; 5,156,833; 5,156,834; 5,281,409; and 5,368,842; incorporated by reference.

A present invention aerosol deodorant-antiperspirant product can include other ingredients such as fragrances, bacteriostats, fungistats, colorants, antiinflammatory agents, antioxidants, and the like.

For example, between about 0.01–0.5 weight percent of a bacteriostat can be included as an optional ingredient. The bacteriostat functions as a deodorant by preventing bacterial generation of malodorous degradation byproducts from perspiration. Typical bacteriostatic compounds include Triclosan (Ciba-Geigy), Chloracel (Reheis Chemical Company), zinc phenolsulfonate, dichloro-m-xylenol, sodium N-lauroyl sarcosine, and the like.

Between about 0.1–2 weight percent of a fragrance can be included as an optional ingredient. The selected fragrance ingredient is one which does not adversely affect the dimensional stability of the aerosol deodorant product, and preferably which contributes an odorant masking effect. Fragrances typically are organic compounds of specific type structures, which include phenolic materials, essential oils, synthetic oils, aldehydes and ketones, polycyclic compounds, esters, and alcohols. Specific fragrances are illustrated by linalyl acetate, isopropyl myristate, cedryl acetate, myrcenyl acetate, and other compounds such as those listed in U.S. Pat. No. 5,114,717; incorporated by reference. The fragrance ingredient can be encapsulated with a film-forming polymer such as polyvinyl acetate.

Between about 0.5–3 weight percent of a binder/carrier type powder can be included as an optional ingredient, such as microcrystalline cellulose, polyacrylamide, talc, calcium carbonate, and the like.

A present invention aerosol deodorant-antiperspirant product can be produced by blending the ingredients in a prescribed order of addition. In a general procedure, a concentrate is prepared by first admixing the volatile oil, suspending agent, antiperspirant, alkali metal bicarbonate, fragrance, and optional additives such as bacteriostat and fragrance ingredients. The concentrate then is milled under high shear conditions, and then charged to an aerosol dispensing container. A valve is crimped to the container, and the propellant is charged to the container under pressure. Procedures for production of pressurized aerosol products are described in publications such as U.S. Pat. Nos. 4,183,911; 4,743,440; 4,935,224; and 5,178,871; incorporated by reference.

The following examples are further illustrative of the present invention. The components and specific ingredients are presented as being typical, and various modifications can be derived in view of the foregoing disclosure within the scope of the invention.

EXAMPLE I

This Example illustrates the particle size distribution of sodium bicarbonate before and after air-jet milling.

Commercial grade sodium bicarbonate (3DF, Church & Dwight) is processed by air-jet milling (Particle Size Technology, Inc.), and the particle size distribution of milled samples is determined in comparison with unmilled samples by means of a Microtrac laser-scattering particle size analyzer.

The 3DF sodium bicarbonate has an average particle size of 31.4 microns, and the micronized 3DF sodium bicarbonate has an average particle size of 9.8 microns.

The middle 80% of particle size distribution is between 15.4 and 55.8 microns for the 3DF sodium bicarbonate, and between 4.3 and 21.5 microns for the micronized form.

EXAMPLE II

This Example illustrates the preparation of aerosol deodorant-antiperspirant compositions in accordance with the present invention.

The invention compositions are formulated with the following ingredients:

| INGREDIENTS | A | B |
|---|---|---|
| Cyclomethicone | 6.0 | 6.0 |
| Diisopropyl adipate | 15.5 | 15.5 |
| Bentone gel VS5PC[1] | 12.5 | 12.5 |
| Reach 103-0[2] | 12.5 | |
| Reach 103[3] | | 12.5 |
| Encapsulated sodium bicarbonate[4] | 2.5 | 2.5 |
| Fragrance[5] | 0.75 | 0.75 |
| 1,1'-difluoroethane | 15 | 15 |
| Butane | 35 | 35 |
| % Sweat reduction | 30 | 37 |

[1]76% cyclomethicone, 18% hydrophobically-modified clay, 5% propylene carbonate; Rheox.
[2]D10 = 10–15 microns; D50 = 25–30 microns; D = 45–55 microns (Maximum = 74 microns); Reheis (Dx = x % of product having particle diameter less than).
[3]D10 = 2–3 microns; D50 = 8–15 microns; D = 20–30 microns (Maximum = 54 microns); Reheis.
[4]Optimax RR; 30 weight % starch coating; average particle size of 30 microns; Encapsulation Technology.
[5]Fresh Scent; Takasago.

A concentrate is formed by admixing the cyclomethicone, clay, diisopropyl adipate, antiperspirant-active, encapsulated sodium bicarbonate and fragrance ingredients, and milling the admixture at high shear (about 1000 psig in a Gaulin Homogenizer).

The concentrate is charged to a standard aerosol can. A valve is mounted and crimped on the can, and the two propellant ingredients are added under pressure.

Wetness Reduction Test

The wetness reduction is evaluated using a standard gravimetric clinical method. In a typical method, 50 test subjects without axillary abnormalities are required to abstain from the use of all antiperspirant materials for at least 2 weeks prior to the test period. On day 1, the test subjects are placed in an environmentally-controlled chamber with a temperature of 100° F. and 35–40% relative humidity. A 40 minute warm-up period after chamber entry is allowed to elapse before beginning the sweat collection. The warm-up period is immediately followed by two 20 minute collection periods in which preweighed absorbent pads are placed under the axilla and kept in position during the test periods. After these collections, the pads are removed, reweighed and the sweat output of each axilla is computed. Subjects with greater than 300 mg sweat output are generally included in the study. During the following three days, the subjects are treated with the antiperspirant product under one arm and no product (control) under the other arm. Twenty four hours following the final application, the sweat output of each axilla is determined by the method described above. Sweat reduction is calculated using the following equation:

Sweat reduction=100(control−product)/control

The comparative data listed above demonstrate that each of invention aerosol formulation A and aerosol formulation B are effective for reducing underarm wetness of human subjects, and that an antiperspirant ingredient with a lesser average particle size provides enhanced activity for wetness reduction.

EXAMPLE III

This Example illustrates the enhancement of sweat reduction activity when an invention aerosol deodorant-antiperspirant composition has a preferred volatile oil/emollient ratio and a particulate antiperspirant with a preferred particle size.

An invention composition is formulated with the following ingredients:

| INGREDIENTS | C |
|---|---|
| Cyclomethicone | 10.7 |
| Diisopropyl adipate | 10.8 |
| Bentone gel[1] | 12.5 |
| Reach 103[2] | 12.5 |
| Encapsulated sodium bicarbonate[3] | 2.5 |
| Fragrance | 1.0 |
| 1,1'-difluoroethane | 15 |
| Butane | 35 |
| % Sweat reduction | 44 |

[1]76% cyclomethicone, 18% hydrophobically modified clay, 5% propylene carbonate; Rheox.
[2]D10 = 2–3 microns; D50 = 8–15 microns; D = 20–30 microns (Maximum = 54 microns); Reheis.
[3]Optimax RR; Encapsulation Technology.

An invention aerosol product is prepared, and sweat reduction is tested, following the procedures of Example II.

In comparison with invention aerosol formulation A and aerosol formulation B of Example II, aerosol formulation C has a preferred ratio of cyclomethicone/diisopropyl adipate, and a particulate antiperspirant with a preferred average particle size, which provide a corresponding enhancement of sweat reduction activity.

EXAMPLE IV

This Example illustrates the sweat reduction properties of an aerosol deodorant-antiperspirant composition not in accordance with the present invention.

An aerosol composition is prepared with the following ingredients:

| INGREDIENTS | D |
|---|---|
| Cyclomethicone | 13.2 |
| Diisopropyl adipate | 8.3 |
| Bentone gel[1] | 12.5 |
| Reach 103-0[2] | 12.5 |
| Encapsulated sodium bicarbonate[3] | 2.5 |
| Fragrance | 0.75 |
| 1,1'-difluoroethane | 15 |
| Butane | 35 |
| % Sweat reduction | 15 |

[1]76% cyclomethicone, 18% hydrophobically modified clay, 5% propylene carbonate; Rheox.
[2]D10 = 10–15 microns; D50 = 25–30 microns; D = 45–55 microns (Maximum = 74 microns); Reheis.
[3]Optimax RR; Encapsulation Technology.

An aerosol product is prepared, and sweat reduction is tested, following the procedures of Example II.

In comparison to the invention aerosol formulations A–C, aerosol formulation D has a diminished sweat reduction activity because of the high cyclomethicone/diisopropyl adipate ratio, and the relatively large average particle size of the particulate antiperspirant ingredient.

EXAMPLE V

This Example illustrates the preparation of effective aerosol deodorant-antiperspirant compositions with different emollient ingredients in accordance with the present invention.

Aerosol products are prepared with the following ingredients:

| INGREDIENTS | E | F | G |
|---|---|---|---|
| Cyclomethicone | 13.2 | 13.2 | 13.2 |
| Isopropyl palmitate | 8.3 | | |
| Isopropylmyristate | | 7.3 | |
| $C_{12}$–$C_{15}$ Alkyl benzoate | | | 7.3 |
| Dimethicone | | 1.0 | 1.0 |
| Bentone gel VS5PC[1] | 12.5 | 12.5 | 12.5 |
| Reach 103[2] | | 12.5 | 12.5 |
| Encapsulated sodium bicarbonate[3] | 2.5 | 2.5 | 2.5 |
| Fragrance | 0.75 | 0.75 | 0.75 |
| 1,1'-difluoroethane | 15 | 15 | 15 |
| Butane | 35 | 35 | 35 |
| % Sweat reduction | 40 | 44 | 44 |

[1]76% cyclomethicone, 18% hydrophobically modified clay, 5% propylene carbonate; Rheox.
[2]D10 = 2–3 microns; D50 = 8–15 microns; D = 20–30 microns (Maximum = 54 microns); Reheis.
[3]Optimax RR; Encapsulation Technology.

Aerosol products are assembled, and sweat reduction is tested, following the procedures of Example II.

What is claimed is:

1. A deodorant-antiperspirant composition in an aerosol dispensing container which comprises (1) between about 1–15 weight percent of particulate alkali metal bicarbonate having an average particle size between about 5–100 microns; (2) between about 5–25 weight percent of particulate antiperspirant ingredient having an average particle size between about 1–40 microns; (3) between about 10–25 weight percent of volatile oil; (4) between about 5–20 weight percent of emollient, and the ratio of volatile oil to emollient is between about 1–2.5:1; (5) between about 0.5–3 weight percent of particulate suspending agent; and (6) between about 10–60 weight percent of aerosol propellant.

2. A deodorant-antiperspirant composition in accordance with claim 1 wherein the alkali metal bicarbonate is sodium bicarbonate or potassium bicarbonate or a mixture thereof.

3. A deodorant-antiperspirant composition in accordance with claim 1 wherein the alkali metal bicarbonate particles are encapsulated with an organic surface coating.

4. A deodorant-antiperspirant composition in accordance with claim 1 wherein the alkali metal bicarbonate particles are encapsulated with a surface coating selected from the group consisting of hydrophilic and hydrophobic film-forming organic ingredients.

5. A deodorant-antiperspirant composition in accordance with claim 1 wherein the alkali metal bicarbonate particles are encapsulated with a polysaccharidic surface coating.

6. A deodorant-antiperspirant composition in accordance with claim 1 wherein the alkali metal bicarbonate ingredient is a mixture of encapsulated and unencapsulated particles.

7. A deodorant-antiperspirant composition in accordance with claim 1 wherein the antiperspirant ingredient has an average particle size in the range between about 10–35 microns.

8. A deodorant-antiperspirant composition in accordance with claim 1 wherein the antiperspirant ingredient comprises an astringent metal salt.

9. A deodorant-antiperspirant composition in accordance with claim 1 wherein the antiperspirant is an ingredient selected from the group consisting of aluminum, zirconium and zinc salts, and mixtures thereof.

10. A deodorant-antiperspirant composition in accordance with claim 1 wherein the volatile oil is selected from the group consisting of silicone and branched-chain hydrocarbon compounds.

11. A deodorant-antiperspirant composition in accordance with claim 1 wherein the volatile oil ingredient comprises a cyclic or linear polydimethylsiloxane containing 3–9 silicon atoms.

12. A deodorant-antiperspirant composition in accordance with claim 1 wherein the volatile oil ingredient comprises a $C_{12}$–$C_{20}$ branched-chain hydrocarbon.

13. A deodorant-antiperspirant composition in accordance with claim 1 wherein the emollient comprises a nonvolatile ester.

14. A deodorant-antiperspirant composition in accordance with claim 1 wherein the emollient comprises a carboxylate ester selected from the group consisting of lactates, citrates, tartrates and adipates.

15. A deodorant-antiperspirant composition in accordance with claim 1 wherein the emollient comprises a nonvolatile silicone.

16. A deodorant-antiperspirant composition in accordance with claim 1 wherein the emollient comprises lanolin.

17. A deodorant-antiperspirant composition in accordance with claim 1 wherein the suspending agent is selected from the group consisting of colloidal clay and silica.

18. A deodorant-antiperspirant composition in accordance with claim 1 wherein the suspending agent is hydrophobic bentonite clay.

19. A deodorant-antiperspirant composition in accordance with claim 1 wherein the suspending agent is hydrophobic hectorite clay.

20. A deodorant-antiperspirant composition in accordance with claim 1 wherein the suspending agent is pyrogenic silica.

21. A deodorant-antiperspirant composition in accordance with claim 1 wherein the aerosol propellant is a liquified normally-gaseous medium selected from the group consisting of hydrocarbons and halogenated hydrocarbons and mixtures thereof.

22. A deodorant-antiperspirant composition in accordance with claim 1 wherein the aerosol propellant is selected from the group consisting of $C_3$–$C_5$ aliphatic hydrocarbons and mixtures thereof.

23. A deodorant-antiperspirant composition in accordance with claim 1 which contains between about 0.01–0.5 weight percent of bacteriostat as an optional ingredient.

24. A deodorant-antiperspirant composition in accordance with claim 1 which contains between about 0.1–2 weight percent of fragrance as an optional ingredient.

25. A deodorant-antiperspirant composition in accordance with claim 1 which contains between about 0.5–3 weight percent of talc or calcium carbonate as an optional ingredient.

26. A deodorant-antiperspirant composition in accordance with claim 1 which contains between about 0.5–3 weight percent of microcrystalline cellulose or starch powder as an optional ingredient.

* * * * *